United States Patent
Sala et al.

(10) Patent No.: US 11,432,987 B2
(45) Date of Patent: Sep. 6, 2022

(54) AMBULATION ASSISTANCE WEARABLE DEVICE AND CORRESPONDING METHOD

(71) Applicants: Nicoló Sala, Gazzaniga (IT); Francesco Rusnati, Bussero (IT); Manuel Rocco, Paderno Dugnano (IT)

(72) Inventors: Nicoló Sala, Gazzaniga (IT); Francesco Rusnati, Bussero (IT); Manuel Rocco, Paderno Dugnano (IT); Davide Russo, Florence (IT); Christian Spreafico, Dalmine (IT); Antonio Caputi, Florence (IT); Paolo Carrara, Val Brembo (IT)

( * ) Notice: Subject to any disclaimer, the term of this patent is extended or adjusted under 35 U.S.C. 154(b) by 379 days.

(21) Appl. No.: 16/753,770

(22) PCT Filed: Oct. 2, 2018

(86) PCT No.: PCT/IB2018/057629
§ 371 (c)(1),
(2) Date: Apr. 4, 2020

(87) PCT Pub. No.: WO2019/069217
PCT Pub. Date: Apr. 11, 2019

(65) Prior Publication Data
US 2020/0276072 A1   Sep. 3, 2020

(30) Foreign Application Priority Data
Oct. 5, 2017   (IT) .................. 102017000111746

(51) Int. Cl.
*A61H 3/00* (2006.01)
*A61B 5/11* (2006.01)
*A61B 5/00* (2006.01)

(52) U.S. Cl.
CPC ............... *A61H 3/00* (2013.01); *A61B 5/112* (2013.01); *A61B 5/6828* (2013.01);
(Continued)

(58) Field of Classification Search
CPC ......... A61H 3/00; A61B 5/112; G09B 19/003
See application file for complete search history.

(56) References Cited

U.S. PATENT DOCUMENTS 5,575,294 A * 11/1996 Perry ....................... A45B 3/00
600/595
2006/0025836 A1   2/2006 Van Gerpen
(Continued)

FOREIGN PATENT DOCUMENTS

EP   3207869   8/2017
WO   2011130223   10/2011

*Primary Examiner* — Noah Chandler Hawk
(74) *Attorney, Agent, or Firm* — Themis Law

(57) ABSTRACT

An ambulation assistance wearable device, and related method, includes a support to be removably attached to the body of a person; a power supply anchored to the support; a light source mounted on the support and electrically connected to the power supply, which is configured to emit a beam of visible light toward the ground; a front stepping point where the person moves the foot to generate a bright spot in that point and move forward along an ambulation direction; a sensor that detects at least one control parameter identifying the ambulation condition; and a processing unit connected to the power supply, the light source and the sensor, which controls the activation-deactivation of the light source as a function of the at least one control parameter. The control parameter corresponds to an angle or a displacement measurement related to the instant position of a part of the body during ambulation.

41 Claims, 8 Drawing Sheets

(52) U.S. Cl.
CPC ........... *A61H 2201/0188* (2013.01); *A61H 2201/5023* (2013.01); *A61H 2201/5069* (2013.01); *A61H 2201/5084* (2013.01)

(56) References Cited

U.S. PATENT DOCUMENTS

| | | |
|---|---|---|
| 2006/0292533 A1 | 12/2006 | Selod |
| 2011/0021320 A1* | 1/2011 | Lenhardt ............... A61H 3/00 434/185 |
| 2016/0262661 A1* | 9/2016 | Sarkar ................ A61B 5/112 |
| 2016/0310341 A1 | 10/2016 | Yu |
| 2017/0116869 A1* | 4/2017 | Pape ..................... G09B 5/02 |
| 2019/0125216 A1* | 5/2019 | Salcido ............... A61B 5/112 |
| 2020/0090545 A1* | 3/2020 | Collin ................... A61H 3/00 |
| 2021/0183263 A1* | 6/2021 | Virgo ................ G09B 19/003 |

\* cited by examiner

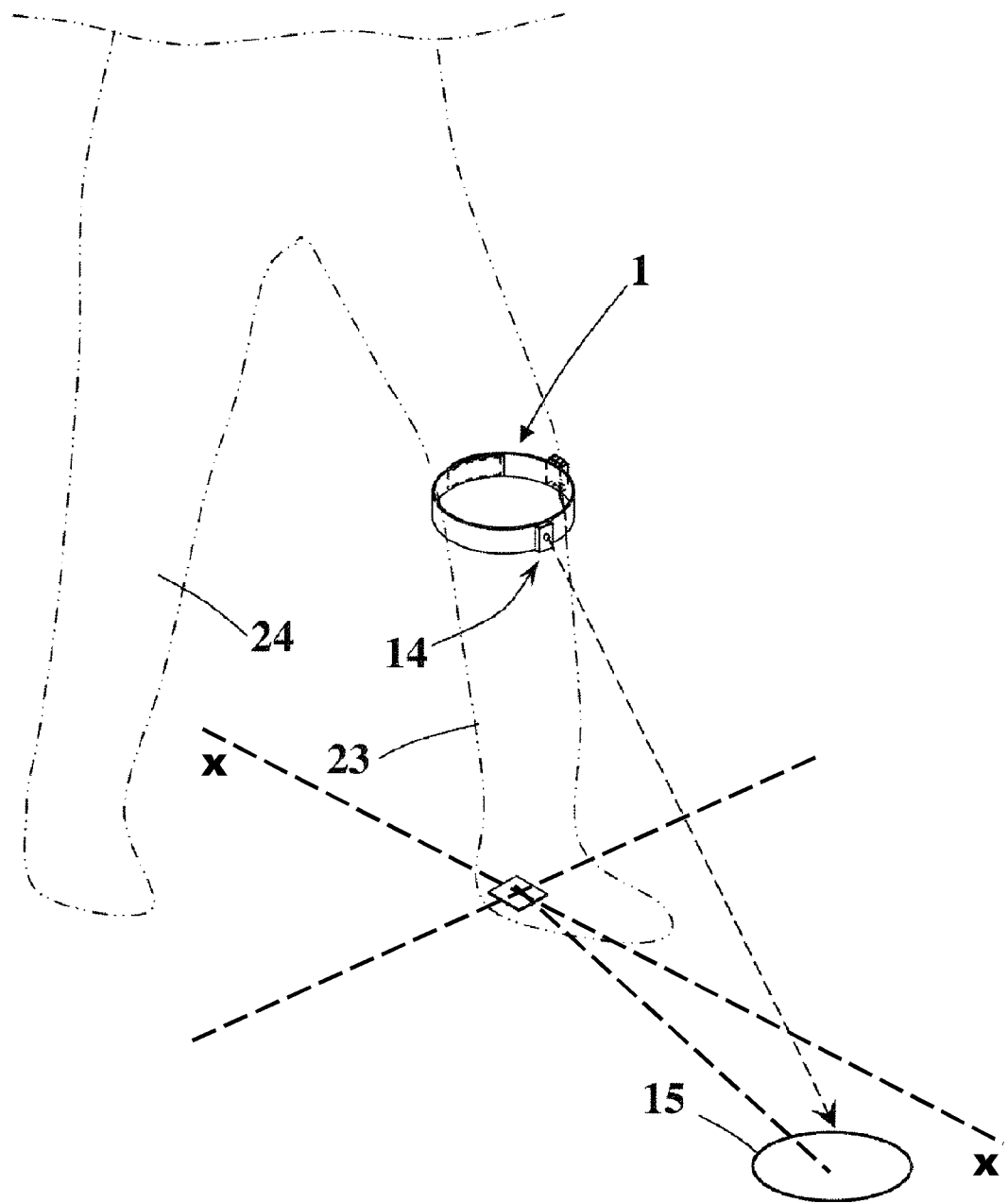
Fig.1 (KNOWN ART)

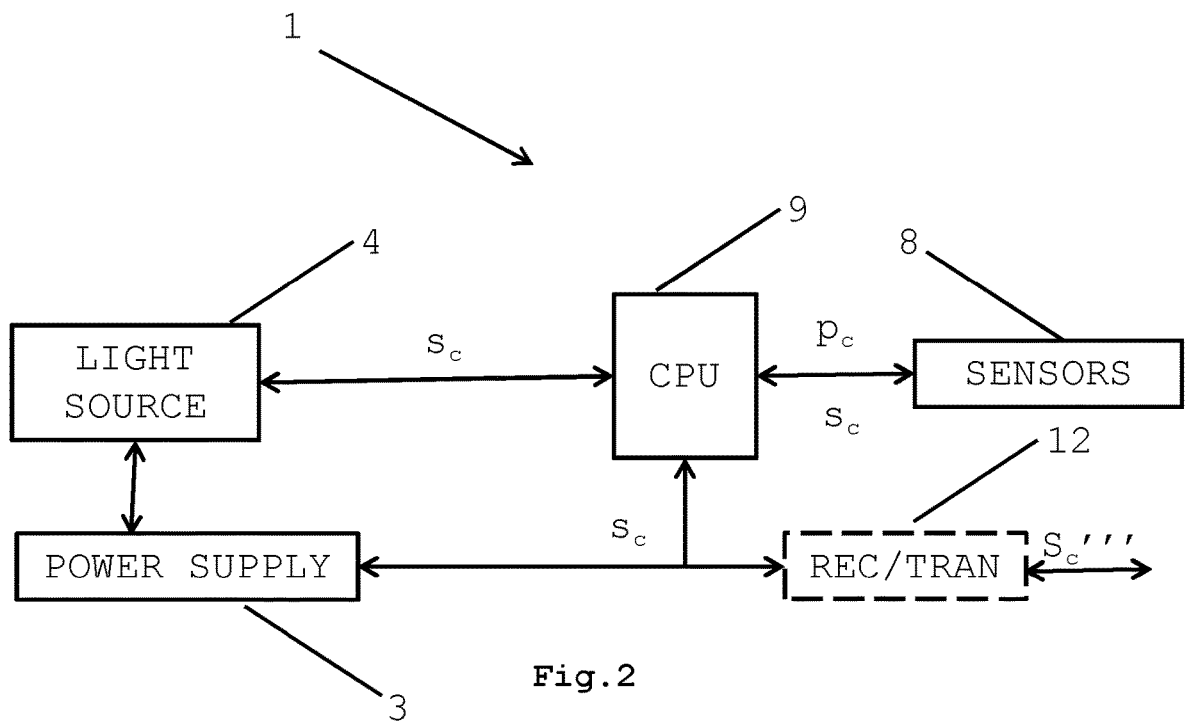
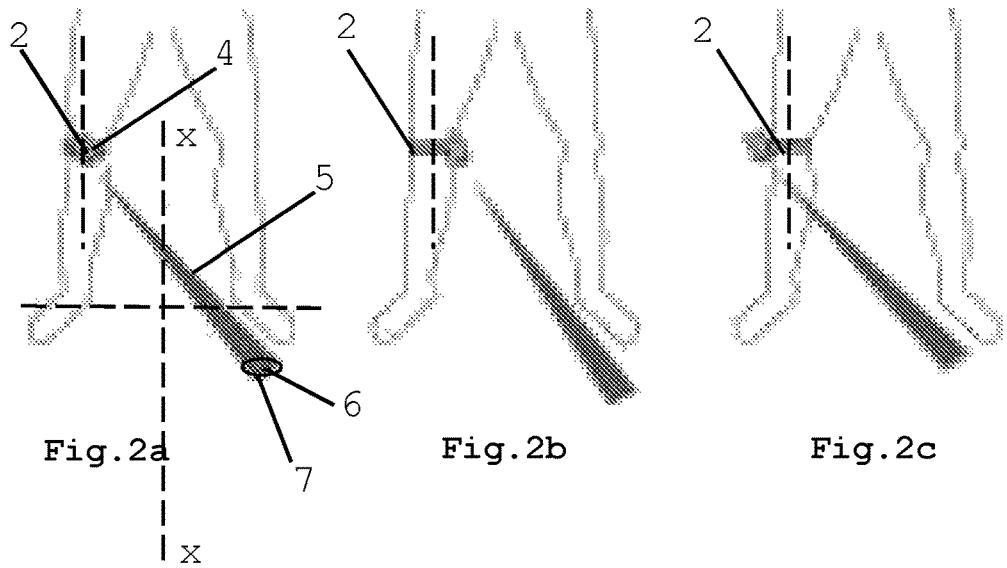

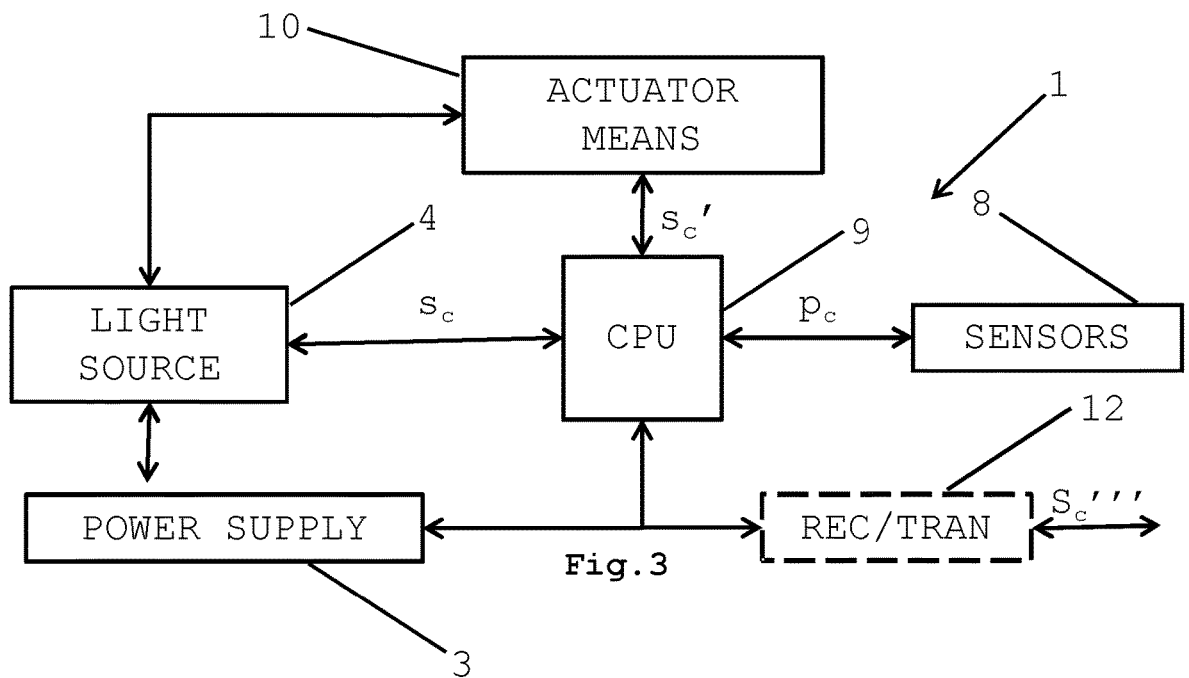
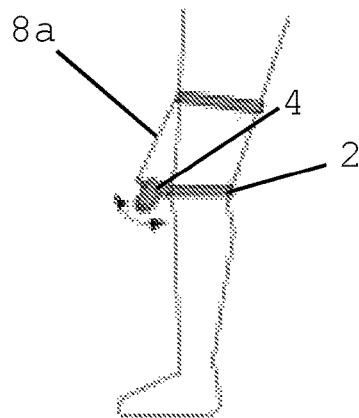
Fig.3a
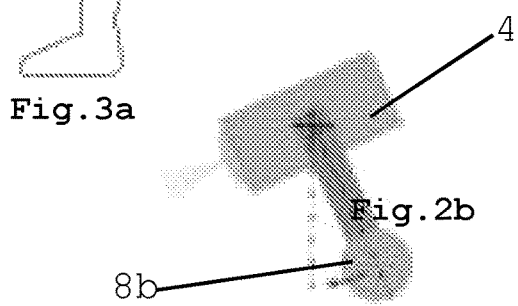
Fig.3b
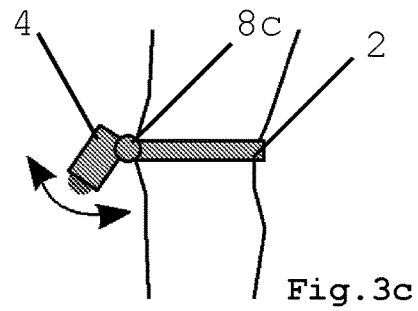
Fig.3c
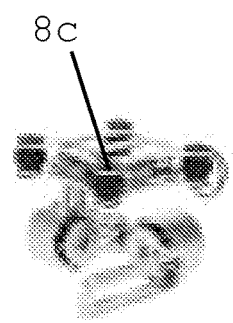
Fig.3d

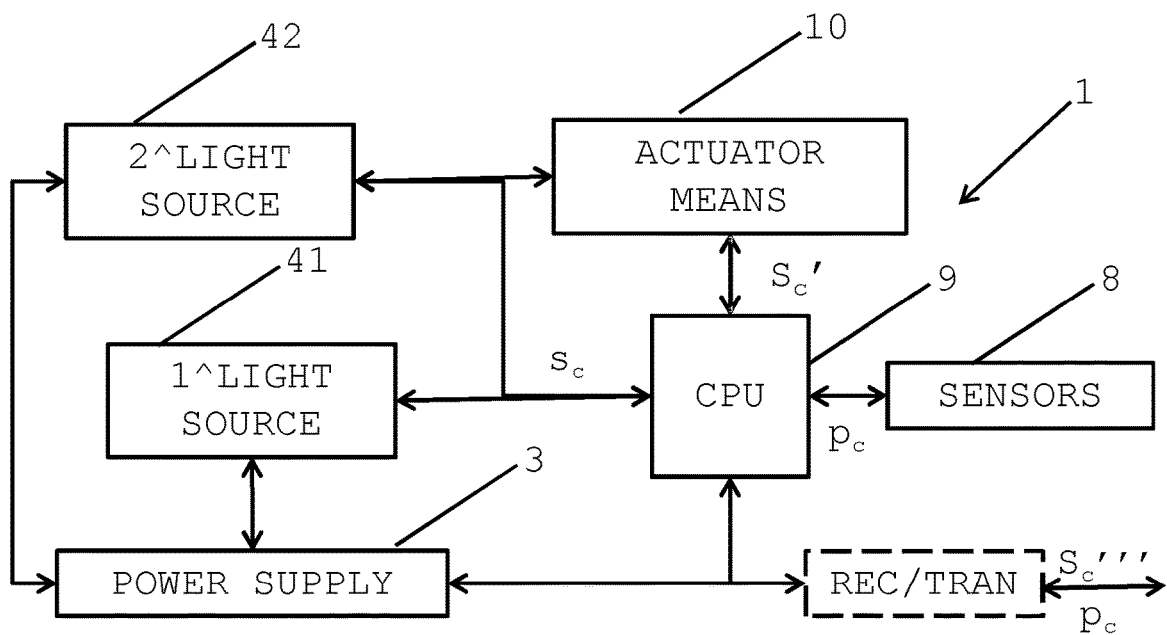
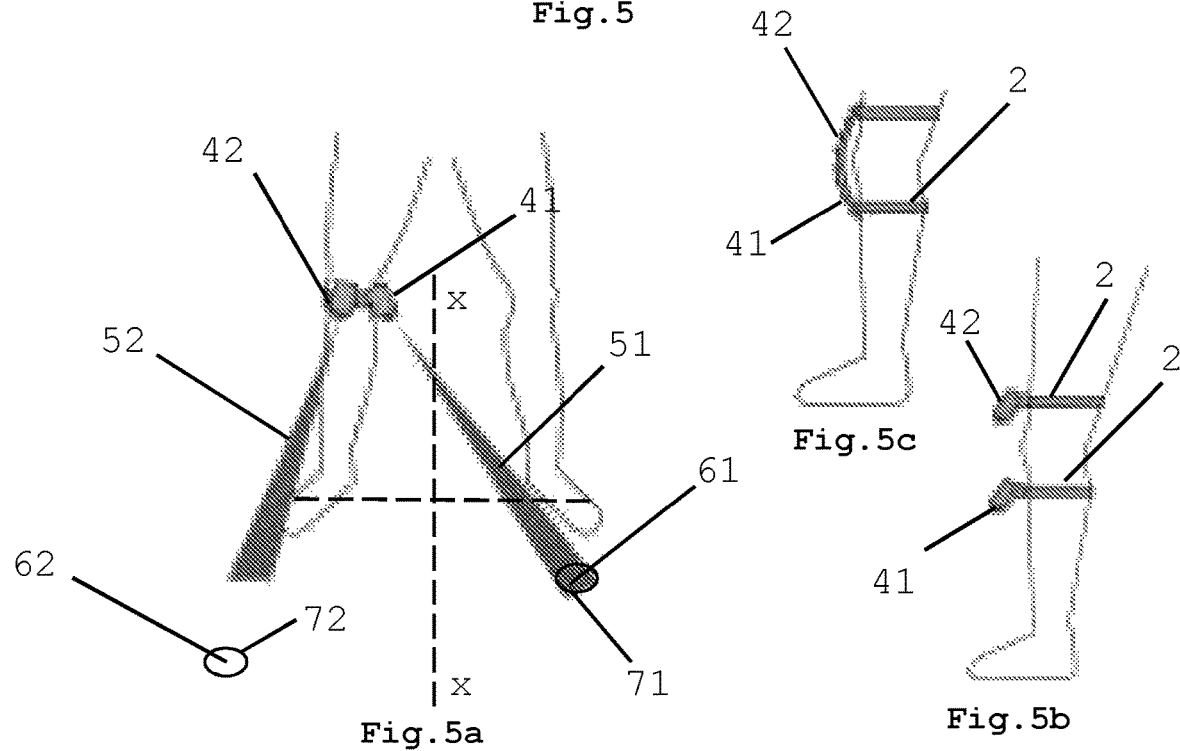
Fig. 5
Fig. 5a   Fig. 5b   Fig. 5c

AMBULATION ASSISTANCE WEARABLE DEVICE AND CORRESPONDING METHOD

Object of the present invention is an ambulation assistance wearable device and a corresponding method according to the preambles of the corresponding independent claims.

The present invention is specifically applicable to the field of the rehabilitation of people with mobility problems, for example, during the recovering step after a surgery or an accident or suffering from medical conditions such as Parkinson's disease or other diseases causing, indeed, mobility problems.

Referring in particular to Parkinson's disease, a common problem affecting people suffering from such a disease is the "freezing", i.e. a disorder whereby a person feels the urge to walk, but can not lift the feet from the ground in order to make steps.

Different devices attempting to solve the "freezing" problem and, more generally the ambulation assistance issue, have been developed over years. Such devices provide for projecting a visible light, also called marker in jargon, to the ground, in front and at some distance from a person. The marker, which a person is asked to pass with a step, has for example the shape of a line perpendicular to the forward direction or any desired additional shape like a bright spot or brighter than the ambulation ground.

The devices generating such a visible light are for example mounted on canes or walking supports supplied to people to be rehabilitated and the distance between the person and the projected marker can be adjusted.

Wearable devices arranged for ambulation assistance, for example the device described in US2016/0310341A1, also exist. Such a device is provided for being worn by a person at a lower limb, in particular at the knee joint and comprises, inter alia, a light source 14 arranged for projecting a light beam towards the ground, in a front stepping area 15 that is angularly offset with respect to the forward direction of the person (axis x-x in FIG. 1 illustrating the known art).

The wearable device described in US2016/0310341A1 thus generates, to the ground, the mark 15 corresponding to the point to which the ambulating person will have to rest the foot opposite to the one of the lower limb supporting the device.

Such a device also comprises an activation unit to activate the light source provided at the sole of the shoe worn by the person at the lower limb supporting the device. The activation unit is intended to detect the pressure exerted thereon by the resting foot, such as to activate the light source when the pressure is larger than zero, i.e. when the foot is on the ground and the person is therefore going to lift the other foot in order to make a step.

All the aforesaid devices suffer from a number of drawbacks.

The non-wearable devices, mounted for example on walking supports or canes, generate to the ground markers whose position on the ground strongly depends on how the walking supports or canes, on which they are mounted, are used, and since often people using such devices are elderly or have reduced mobility, the stability of the marker to the ground is impaired, i.e. the marker can not be held in a precise point or area of the ground during ambulation and, in particular, in the time period in which a person lifts his/her own foot to pass such a marker.

As regard to the wearable devices, and more specifically the device described in US2016/0310341A1 but also other known devices, these are not able to generate a mark to the ground, that remains steady (i.e. still in a precise point or area of the ground) during the ambulation, in the time period wherein a person lifts his/her own foot in order to reach such a mark therewith. This drawback prevented known systems, such for example those described in documents US2016/310341, US2006/025836, US2006/292533, WO2011/130223 and EP3027869, from finding practical application and popularity among the users. In fact, the position sensitivity of the bright spot and the little stability thereof, also due to changes in ambulation over time, made very difficult for the users to concentrate on the lightened zone that does not remain steady on the ground and therefore the use of the devices did not facilitate the proper ambulation and the user following the lightened zone became very tired from both the physical and thus muscular, and the intellectual effort points of view.

In the field of motor rehabilitation and new posture setting, known devices did not go beyond an experimental application and have never become finished mass-produced products.

As from the document US2016/310341 it is evident that such a device is further provided for rehabilitating only one lower limb (that opposite to the one on which the device is mounted). Therefore for a whole rehabilitation two devices are required, to be worn one on each lower limb.

Not only, in order to change the step distance (i.e. the distance between the person and the mark projected by each device), the device taught in US2016/0310341A1 requires the position at which the device itself is attached to the lower limb, for example comprised between knee and hip, to be changed. Therefore the adjustment of the distance of the mark projected to the ground, with respect to the person to be rehabilitated, can become laborious and can not be done in real time, i.e. during ambulation.

Therefore there is the need for improving the state of the art in the field of the ambulation assistance, in order to solve the afore mentioned drawbacks.

Therefore the main object of the present invention is to provide an ambulation assistance wearable device and a corresponding method, which allow precisely stabilizing a mark projected to the ground, independently of the movement made by the person wearing the same.

Another object of the present invention is to provide an ambulation assistance wearable device and a corresponding method, which are able to rehabilitate both the lower limbs of a person.

Still another object of the present invention is to provide an ambulation assistance wearable device and a corresponding method, which allow easily adjusting the distance between the person and the mark projected to the ground, also during ambulation.

Still another object of the present invention is to provide an ambulation assistance wearable device and a corresponding method which are easy to make/implement.

The invention achieves the above objects with an ambulation assistance wearable device according to claim 1.

A preferred embodiment of the invention provides that the light source is displaceable mounted according to at least one degree of freedom and that changes at least the direction of propagation of the light beam emitted, said displacement being controlled by an electric motor controlled by a control unit generating signals to operate said motor as a function of the said at least one control parameter of the position in the space of said light source.

In particular, the support of the light source is of spherical type or however a support allowing said light source to swing along two, preferably three axes.

Such supports are known to the person skilled in the art in many configurations and implementation variations and can be easily found in the market.

Different types of sensors of the light source position in the space can be provided.

A preferred embodiment provides for measuring the changes of the light source position in the space, i.e. tracking over time the position of said light source and generating the control signals for activating the motor as a function of said signals for detecting the change of position of the light source in the space, such as to compensate for the displacement of the mark generated by the light source by said position changes.

In order to obtain the required speed of action, according to a preferred embodiment the invention provides for combining a sensor of the type called MEMS with each light source.

Such a sensor provides for detecting the position changes of an object in the space thanks to the combination of at least one accelerometer and one gyroscope.

The MEMS type sensors detect a capacitive electric signal variable as a function of the mutual displacement between the faces of a capacitor when they are inertially stressed, for example in the present instance upon the movement of the limb inside a gravitational field.

Said capacitor faces are conductive foils attached by a spring.

In an embodiment, the sensor measures the angular velocities of rotation of the three angles (degrees per second).

It is apparent that this type of sensor not only allows the limb movement to be detected as a function of the displacements the limb makes in normal ambulation, but generates a displacement signal also as a function of the movements that are not related to ambulation, such as for example shaking, improper movements of limb rotation, and so forth.

This embodiment therefore not only provides the MEMS sensor to stabilize the footprint of the beam of the light source to the ground, due to side effects related to the ambulation movement, but can optionally and advantageously also constitute the sensor means intended to detect at least one control parameter (pc) identifying the ambulation condition.

It is therefore apparent that the aforesaid embodiment in one or more of its variations can be provided in combination with further sensors intended to detect at least one control parameter (pc) identifying the ambulation condition, such as for example one of the sensors or a combination of said sensors described in one or more of the additional implementation variations in the following described and/or claimed in the dependent claims.

MEMS sensors are devices integrating mechanical elements in a silicon substrate having typical size of 1-10 μm, by combining the computational ability of the microelectronics with that of controlling the micro-sensors and micro-actuators for the design of smart products. MEMS technology comprises accelerometers, gyroscopes, piezoelectric devices and microphones, just to mention a few.

According to a further aspect an ambulation assistance method is provided according to claim 32.

These and still other objects of the present invention will be more evident from the following description of some exemplary embodiments illustrated in the accompanying drawings wherein:

FIG. 1 shows an ambulation assistance wearable device according to the known art;

FIG. 2 shows a block diagram of the main components of a first embodiment of an ambulation assistance device, according to the present invention;

FIGS. 2a, 2b and 2c show some possible mounting positions of the device of FIG. 2;

FIG. 3 illustrates a block diagram of the main components of a second embodiment of an ambulation assistance device, according to the present invention;

FIGS. 3a to 3d show some embodiment variations of the actuator means illustrated in FIG. 3;

FIG. 5 illustrates a block diagram of the main components of a fourth embodiment of an ambulation assistance device, according to the present invention;

FIGS. 5a to 5c show some embodiment variations of the device of FIG. 5;

Figure 4:
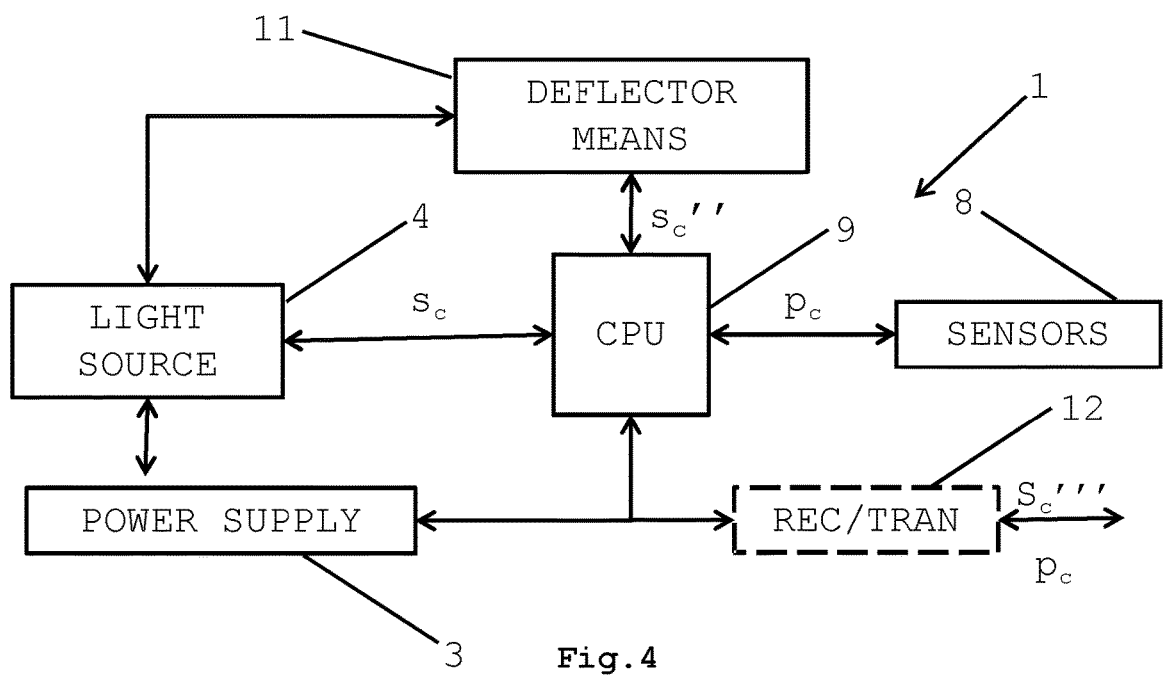
FIG. 4 shows a block diagram of the main components of a third embodiment of an ambulation assistance device, according to the present invention.

Now, in reference to FIGS. 2 to 5c, it will be noted how an ambulation assistance wearable device, according to the present invention, is generally denoted by the numeral reference 1 and comprises at least one support 2 intended to be removably attached to the body of a person, in a respective attachment position, and at least power supply means 3 anchored to such a support 2.

The support 2 according to the present invention can for example be a belt, a band of any suitable type, that may be anchored to the body of a person.

According to a particularly advantageous aspect of the present invention, the support 2 of the device is a kneepad to be worn, for example, over the trousers and intended to wrap the knee joint of the person wearing it.

The power supply unit 3 is provided of any suitable type, for example a rechargeable battery and/or a case for non-rechargeable batteries and/or photovoltaic cells or other systems for generating electric energy and which power supply unit 3 is intended to power supply the other components of the device 1 according to the invention.

The device 1, in fact, also comprises a light source 4 mounted on the support 2 and electrically connected to the power supply means 3, which source is intended, in use, to emit at least one beam of visible light 5 towards the ground, at least at one front stepping point 6. The front stepping point 6 is a point on the ground, to which the person has to move the foot used in that moment in ambulation, to move forward along a forward direction x-x.

In reference specifically to the light source 4 and the beam of visible light 5, it will be noted that the light source 4 can be a laser source, an incandescent electric bulb or a light source provided with one or more leds in combination with fixed or variable optical devices for focusing the light beam, which are able to project a monochromatic or polychromatic or colored light towards the ground, thus defining a mark 7, a spot or the like having higher brightness than the surrounding surfaces and which mark constitutes or comprises the front stepping point 6.

The mark 7 can have circular configuration or can be shaped as a foot sole (right or left as appropriate) or in any desired way.

Advantageously, the device 1 according to the present invention comprises at least sensor means 8 intended to detect at least one control parameter ($p_c$) identifying the ambulation condition.

Such sensor means 8 are of any suitable type and comprise, for example, accelerometers, gyroscopes or magnetometers or combination thereof and other sensors such as for example proximity sensors between two zones of the body which mutually move relatively during ambulation according to a cyclic and substantially repetitive mode and thanks to which the change of position during the ambulation can be determined and the ambulation condition can be extrapolated. They are advantageously mounted on the device 1 and arranged for sending, in use, the at least one control parameter $p_c$ to at least one processing unit 9, which is also comprised in the device 1 of the present invention. The processing unit 9, which is optionally supported by the support 2, is operatively connected, in a way known to the person skilled in the art, to the other elements of the device, i.e. at least to the power supply means 3, to at least one light source 4 and said at least sensor means 8, and it exchanges suitable control signals $s_c$ with the latter.

The processing unit 9 is intended, in use, to control the activation-deactivation of said at least one light source 4 as a function of said at least one control parameter $p_c$ detected by the sensor means 3.

Advantageously, the control parameter $p_c$ is at least one parameter corresponding to an angle or a displacement measurement related to the instant position or to an average value typical for the subject or generated by measurements on several different subjects, of at least one part of the body of the person which, during ambulation, wears the device 1.

Still more advantageously, the body part concerned can be a lower limb of the body and the control parameter $p_c$ can be an angle identifying, instant by instant, the position of such a lower limb, for example based on the mutual position between femur and tibia of the limb, during ambulation.

According to a variation which will be better described in the following, the body part concerned can be the waist or torso of a person and the control parameter $p_c$ can be the measurement of a distance identifying, instant by instant, the moving forward of the waist or torso of the person, along a forward direction, during ambulation.

It will be noted that such an angle or such a distance can be acquired, by means of the afore denoted sensors, in one or more ways that are part of the basic knowledge of the person skilled in the art, whereby, in the present application, the acquisition of the control parameter $p_c$ will not be discussed further.

That said, according to a first embodiment of the present invention, wherein the body part supporting the device 1 is a lower limb, the light source 4 is rigidly attached to the support 2 and intended, in use, to project the at least one beam of visible light 5 at one front stepping point 6 to the ground, to which the foot opposite, with respect to the one of the lower limb supporting the device (see for example FIG. 2a), has to be moved.

In other words, according to the first embodiment of the present invention, the beam of visible light 5 propagates frontally along a plane crossing the knee joint of the limb supporting the device 1 and diagonal with respect to the forward direction x-x, thus projecting a mark 7 for the limb opposite to the one supporting the device.

The activation of the beam of visible light 5, by the processing unit 9, will depend on the value taken instant by instant by the control parameter $p_c$ and will substantially occur when the angle between femur and tibia has reached a preset empirically determined value, for example a maximum value, i.e. when the person wearing the device 1 is going to make a step to move forward with the opposite lower limb. Once the person has reached the mark 7 and tramples on it, based on the value of the parameter $p_c$, the light source 4 will be deactivated, the lightening of the just trampled on mark not being required anymore. The light source of the device 1 worn by a limb will become active again to project a new mark 7 when the control parameter $p_c$ will be such to describe an ambulation condition that provides the execution of a second additional step with the foot with which the mark 7 projected by the device is combined. In order to project two marks 7, each for one of the two feet, each limb or leg is needed to carry a corresponding device. In this case the alternated activation of the two light sources to project the mark 7 related to the relative foot will be ensured in fact by the corresponding control parameter Pc.

As it is known, the mark 7 generated by the beam of visible light 5 according to this first embodiment is a quite steady mark, meaning that it does not move much, on the ground, in the time period in which the person wearing the device 1 lifts the foot to trample on it. This is due to the fact that the knee joint, during the ambulation on a plane, is not subjected to too high movements with respect to the ground and, in particular, the knee joint of the lower limb on which the device 1 is mounted, in use, remains substantially still during the moving forward of the opposite limb.

According to some variations of the first embodiment of the present invention, the light source 4 of the device 1 can be attached to the support 2 such to be in a substantially external lateral position (FIG. 2c) or substantially internal lateral position (FIG. 2b), with respect to a sagittal plane of symmetry of the knee joint on which the device 1 is mounted, or it can also be substantially at such sagittal plane of symmetry (FIG. 2a).

Now, a second embodiment of the device 1 of the present invention (see FIGS. 3 to 3d) comprises at least one light source 4 movably mounted with respect to the at least one support 2, which is able to project the at least one beam of visible light 5 at a front stepping point 4, to the ground, to which the foot of the lower limb supporting the device 1 has to be moved.

In this regard, the device 1 according to the second embodiment of the present invention comprises at least actuator means 10 operatively connected to the at least one processing unit 9 and to the light source 4 and which are intended, in use, to displace the at least one light source 4 in a plane substantially perpendicular to the ground, crossing the knee joint and parallel to the forward direction x-x.

The actuator means 10 can be of active or passive type and, in reference specifically to the passive type actuator means, they comprise at least one rope (8a, in FIG. 3a) and/or at least one spring element (not shown in the drawings), each one constrained, on a side, to the at least one light source 4 and, on the other side, to the waist or thigh of the limb supporting the device 1.

In this context, the light source 4 is rotatably supported by the support 2 about an axis parallel to an axis substantially transversal of such a knee joint and, thus, automatically displaceable as a function of the position of the femur, for example with respect to an axis perpendicular to the ground, during ambulation, as a result of the constraint made by the rope and/or the spring element.

According to a variation of the passive actuator means, since the light source 4 is rotatably mounted as afore described, they comprise at least one mass 8b (FIG. 3b) supported on the bottom by such at least one light source 4, such that the light source 4 is automatically displaceable, as a result of the gravitational force, during ambulation.

The active actuator means 10 of the device according to the invention comprise instead at least one servo-assisted assembly 8c (see FIGS. 3c and 3d) between said at least one support 2 and said at least one light source 4, which is arranged for displacing the at least one light source 4 as a function of a control parameter $p_c$ sent by the at least one processing unit 9 and detected by the sensor means 3.

The control parameter $p_c$ can be the same parameter used for activating-deactivating the light source, possibly further processed by the processing unit 9.

According to an advantageous aspect of the present invention, such a control parameter $p_c$ is a parameter indicating the rotation of the femur with respect to an axis perpendicular to the ground.

As regard to the servo-assisted assembly 8c, it can comprise for example at least two brushless motors connected to the light source 4 in any suitable way and intended to displace such a source as a function of the control parameter $p_c$ and corresponding control signals $s_c$ sent by the processing unit 9.

In the specific instance of the servo-assisted assembly 8c, the light source 4 is also displaceable along a transverse plane parallel to the transverse plane of the knee joint or parallel to the ground of the lower limb supporting the device 1. In this case the detected control parameter $p_c$, as a function of which a control signal $s_c$ for the group 8c is processed by the processing unit 9, is a parameter indicating the instant torsion between femur and tibia and/or the instant lateral yielding of the knee joint.

Now then, as it will be noted, the actuator means allow a steady mark 7 to be projected to the ground, for moving forward the limb supporting the device 1 according to the invention. In other words, the beam of visible light 5 emitted by the light source 4 extends along a plane crossing the knee joint of the limb supporting the device 1 and parallel to the forward direction x-x. The mark 7 that is obtained is steady to the ground, since the light source 4 is forced, by the afore described actuator means, to remain pointed towards the ground and towards the front stepping point 6, independently of the movement of the lower limb supporting the device, during the ambulation, in the time period in which the person makes a step in the forward direction.

Similarly to the first embodiment according to FIGS. 2, 2a to 2c, once the person has reached the mark 7 and tramples on it, based on the value of the parameter pc, the light source 4 will be deactivated, the lightening of the just trampled on mark not being required anymore. The light source of the device 1 worn by a limb will become active again to project a new mark 7 when the control parameter $p_c$ will be such to describe an ambulation condition which provides the execution of a second additional step with the foot with which the mark 7 projected by the device is combined. In order to project two marks 7, each for one of the two feet, each limb or leg is needed to carry a corresponding device. In this case the alternated activation of the two light sources to project the mark 7 related to the relative foot will be ensured in fact by the corresponding control parameter Pc.

Alternatively, according to a third embodiment of the present invention (see FIGS. 4 to 4b), the light source 4 of the afore described device 1 can be rigidly attached to the respective support 2 and the device 1 comprises, instead of the actuator means 10, at least deflector means 11 to deflect the beam of visible light 5 emitted by the light source 4, which are intended to deflect such a beam 5 such that it can be projected to the ground along a plane crossing the knee joint of the limb supporting the device 1 and parallel to the forward direction x-x.

In other words, also this third embodiment allows a mark for moving forward the foot supporting the device 1 to be projected.

The deflector means 11 comprise at least one system of lenses and/or mirrors intended to receive the at least one beam of visible light 5 emitted by the at least one light source 4 and to transmit it towards the ground by dynamically and automatically changing the direction such that it remains still, in the time period in which the person makes a step in the forward direction.

The deflector means 11, in fact, are operatively connected to the processing unit 9 and orientable as a function of a control parameter $p_c$ transmitted by the processing unit 9 in the form of any suitable control signal ($s_c''$).

Also in this case, the control parameter $p_c$ can be the same parameter used for activating-deactivating the light source 4, possibly further processed by the processing unit 9.

According to an advantageous aspect of the present invention, such a control parameter $p_c$ is a parameter indicating the rotation of the femur with respect to an axis perpendicular to the ground.

The deflection means 11 can be provided internally or externally to the light source 4 and can comprise, for example, an orientable mirror (by the unit 9 by sending suitable control signals) inside or outside the source (see the element 11a of FIG. 4a) and/or a mask or screen outside the light source 4, which is orientable in a controlled way by the unit 9, so that to partially dynamically cover the beam of visible light 5 in order to control the portion of beam of visible light 5 that effectively can, in use, reach the ground. Alternatively, the deflector means 11 can comprise an image projector (denoted by numeral reference 11b in FIG. 4b) that, as a function of the control parameter $p_c$ detected by the sensor means, can project different images depending on the position of the limb on which the device 1 is mounted, so that the mark 7 is always in the same position on the ground, in the time period in which the person lifts the limb supporting the device 1 for making a step forward.

Figures 4A, 4B, 4C:
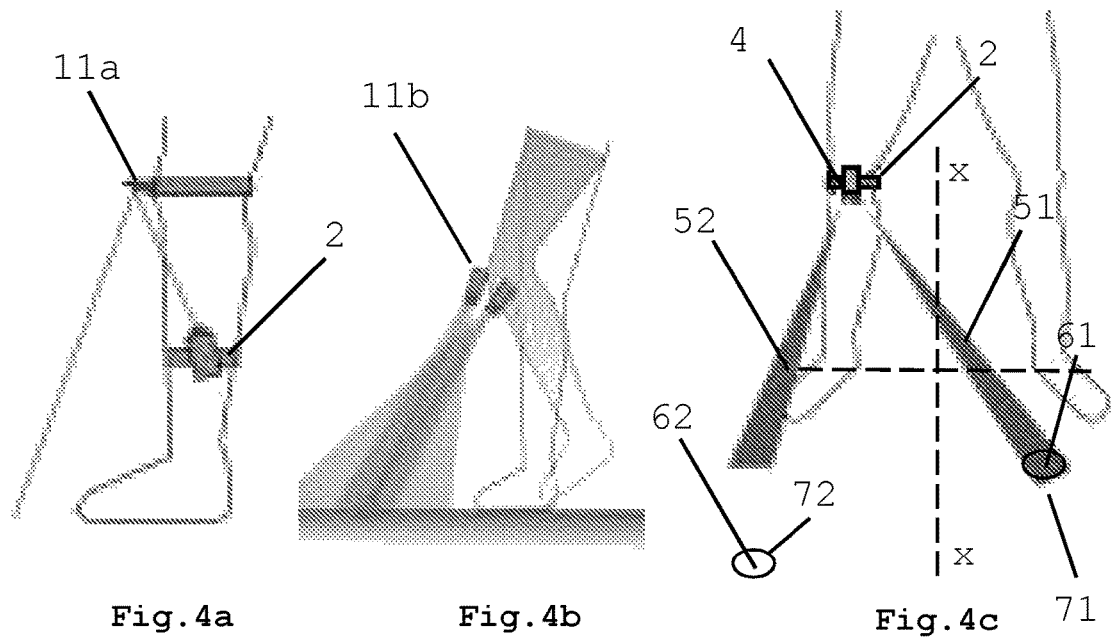
FIGS. 4a to 4c show some embodiment variations of the deflector means illustrated in FIG. 4.

In fact, with particular reference to FIG. 4b, it can be observed that the direction of the beam of visible light 5 changes according to the position of the lower limb on which the device is supported, this because, according to the invention, it is also taken into account that the light source 4 moves forward (i.e. gets closer to the mark 7), while stepping forward towards a mark 7 projected to the ground.

Also in this case, the mark 7 obtained on the ground is steady, since the light source 4 is forced, by the afore described deflector means 11, to remain pointed towards the ground substantially at the front stepping point 64, despite the movement of the lower limb supporting the device 1, in the time period in which the person makes a step in the forward direction.

Now, the afore described deflector means can be used alone or grouped and are advantageously orientable so that said at least one beam of visible light 5 is splittable, as illustrated in FIG. 4c, in:

a first beam 51 that can be projected to the ground at a first front stepping point 61, corresponding to the point to which the person has to move the foot opposite to the one of the lower limb supporting the device 1, and a second beam 52 that can be projected to the ground at a second front stepping point 62, corresponding to the point to which said person has to move the foot of the lower limb supporting said device 1.

This way, a single light source mounted on a single device applied to a lower limb of a person, allows the marks 71, 72 to be emitted in order to support the ambulation of both the lower limbs. That is, on the contrary to the known art, two devices (one to be mounted on each lower limb) projecting to the ground, each one independently, beams of visible light each one dedicated to a single lower limb, are no longer required to be provided.

As it can be noted from FIG. 4c, the first beam 51 extends along a plane crossing the knee joint of the limb supporting the device 1 and diagonal to the forward direction x-x and the second beam 52 extends along a plane crossing the knee joint of the limb supporting the device 1 and parallel to the forward direction x-x.

The first beam 51 and the second beam 52 can be projected alternatively, as a function of at least one further control parameter $p_c$ equal or different from the afore described ones and indicating the flexion of the joint of the knee of the limb supporting the device 1. This way, when a foot reaches a mark 71 at the front stepping point 61, obtained for example by the first beam 51, the deflector means are oriented in order to emit the second beam 52 producing to the ground another mark 72 at the front stepping point 62, which will have to be reached by the other foot.

A fourth embodiment of the device 1 according to the present invention is provided, wherein the device 1 is provided, inter alia, with at least one first light source 41 and at least one second light source 42.

The first light source 41 is rigidly attached to the support 2, as in the first embodiment example afore described, and is arranged for generating a corresponding beam of visible light 51 that can be projected to the ground on a first front stepping point 61, along a plane crossing the knee joint of the limb supporting the device 1 and diagonal to the forward direction x-x. The point 61 corresponds to the point on which the person has to move the foot opposite to the one of the lower limb supporting the device 1.

The second light source 42 is instead movably mounted to the support 2, as in the second exemplary embodiment afore described, and is arranged for generating a corresponding beam of visible light 52 that can be projected to the ground in a first front stepping point 62, along a plane crossing the knee joint of the limb supporting the device 1 and parallel to the forward direction x-x. The point 62 corresponds to the point to which the person has to move the foot of the lower limb supporting the device 1.

Optionally, see FIG. 5b, the first light source 41 and the second light source 42 are mounted on the support 2 such to be, in use, arranged on opposite band with respect to the knee joint of the lower limb of the person wearing the device 1, one mounted at a proximal length of the tibia and the other one at a distal length of the femur.

According to another variation illustrated in FIG. 5c, the first light source 41 and the second light source 42 are comprised in, or each one comprise a led strip.

Also in this case, the two light sources 41 and 42 allow, with a single device 1, the marks 71, 72 assisting the ambulation of both the lower limbs to be emitted. That is, on the contrary to the known art, two devices (one to be mounted on each lower limb) projecting to the ground, each one independently, beams of visible light each one dedicated to a single lower limb, are no longer required to be provided.

The first beam 51 and the second beam 52 can be projected alternatively, as a function of at least one further control parameter equal or different from the afore described ones and indicating the instant position of the knee joint of the limb supporting the device 1. This way, when a foot reaches a mark 71 at the front stepping point 61, obtained for example by the first beam 51, the first light source 41 is deactivated by the processing unit 9 and the second light source 42 is activated in the afore described way, such that the second beam 52 can reproduce to the ground the other mark 72 at the front stepping point 62, that will have to be reached by the other foot.

Figures 6A, 6B:
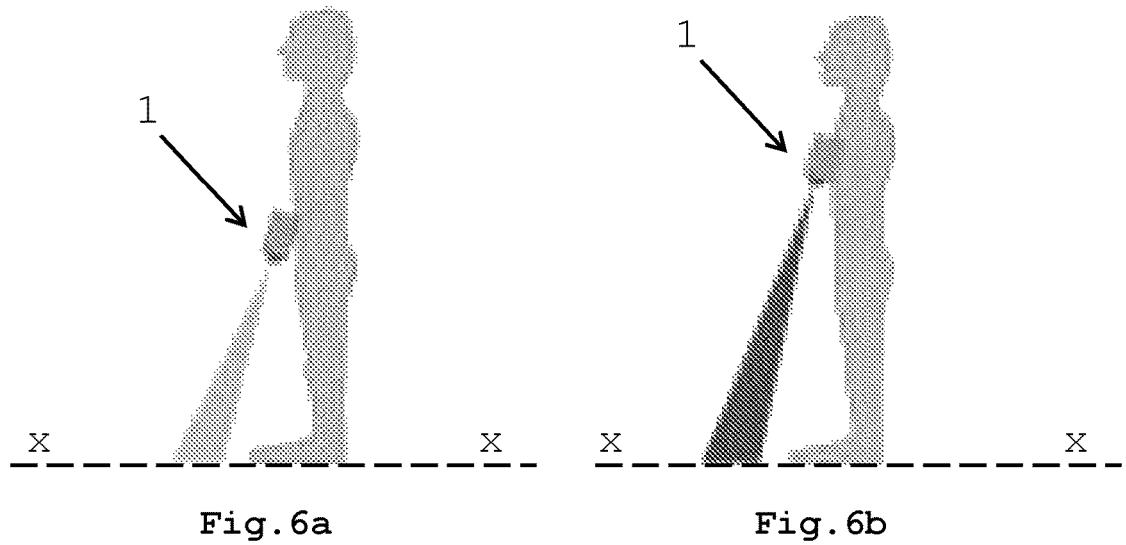
FIGS. 6a and 6b show a fifth embodiment of the device according to the present invention.

Now, a further embodiment of the device 1 according to the present invention provides that the support 2 of the device is designed so that to be attachable to the body of a person, for example to the waist or at the torso, and that the sensor means (8) intended to detect at least one control parameter $p_c$ are sensor means metering the instant displacement of the torso or waist of said person, along the forward direction x-x, during the ambulation (see FIGS. 6a and 6b).

The attaching position of the device 1 according to this embodiment is a substantially central position at the waist or torso of a person, optionally crossing a sagittal plane of symmetry of the body of such a person.

The light source 4 can be rigidly connected to the support 2 or movably mounted with respect thereto and is arranged for emitting at least one beam of visible light 5 towards at least one front stepping point 6 corresponding to the point to which the person has, in use during ambulation, to move a foot.

Such a front stepping point 6 is comprised inside a mark 7 generated by said at least one beam of visible light 5, which mark has advantageously a circular shape symmetrically arranged along the forward direction x-x.

The mark 7 extends to the ground, frontally and transversally with respect to the person wearing the device, such to cover an area that, in use, comprises the front stepping point provided for each lower limb.

The front stepping point 6 is included in the mark 7 and laterally displaced to the right or the left of the forward direction x-x of the person wearing the device, according to the ambulation step considered.

The device according to this embodiment comprises at least actuator means (10) as afore described, which are operatively connected to the processing unit 9 and the light source 4 and intended, in use, to displace the light source 4 at least along the plane perpendicular to the ground and crossing the forward direction x-x.

The device according to this embodiment comprises at least deflector means 11 of the at least one beam of visible light 5 as afore described and intended to receive at least one beam of visible light 5 emitted by the light source 4 and to transmit it towards the ground. The deflector means 11 are operatively connected to the processing unit 9 and orientable as a function of a control parameter $p_c$ transmitted by the processing unit 9.

A typical control parameter $p_c$ is indicating the rotation of the femur with respect to an axis perpendicular to the ground and/or a measurement of the instant displacement of the torso or waist of the person wearing the device.

In this context, the activation-deactivation of the light source 4 provides for lightning for example in a different way (with different colors) zones or sectors of the circular mark 7, at a respective front stepping point, depending on the position of the body of the person wearing the device 1 during ambulation, i.e. according to the step of ambulation in which he/she is.

So for example, a left sector of the mark 7 placed in front of the person can be provided to be colored with a particular color, when the person is going to move forward with the left foot and, vice versa, a right sector of the mark 7 can be provided to be lightened with a particular color (equal or different form the first one), when the person is going to move forward with the right foot.

Now, the device 1 according to the present invention optionally comprises at least one transceiver unit 12 operatively connected to said at least one processing unit 9 and arranged for receiving and transmitting control signals $s_c'''$ and/or the control parameter $p_c$ to/from at least one remote control unit (not shown in the figures).

Such a remote control unit can comprise, for example, databases that can be related to at least one control parameter $p_c$ detected by the sensor means and can process, based on a possible correlation, control signals suitable for the processing unit 9.

Figure 7:
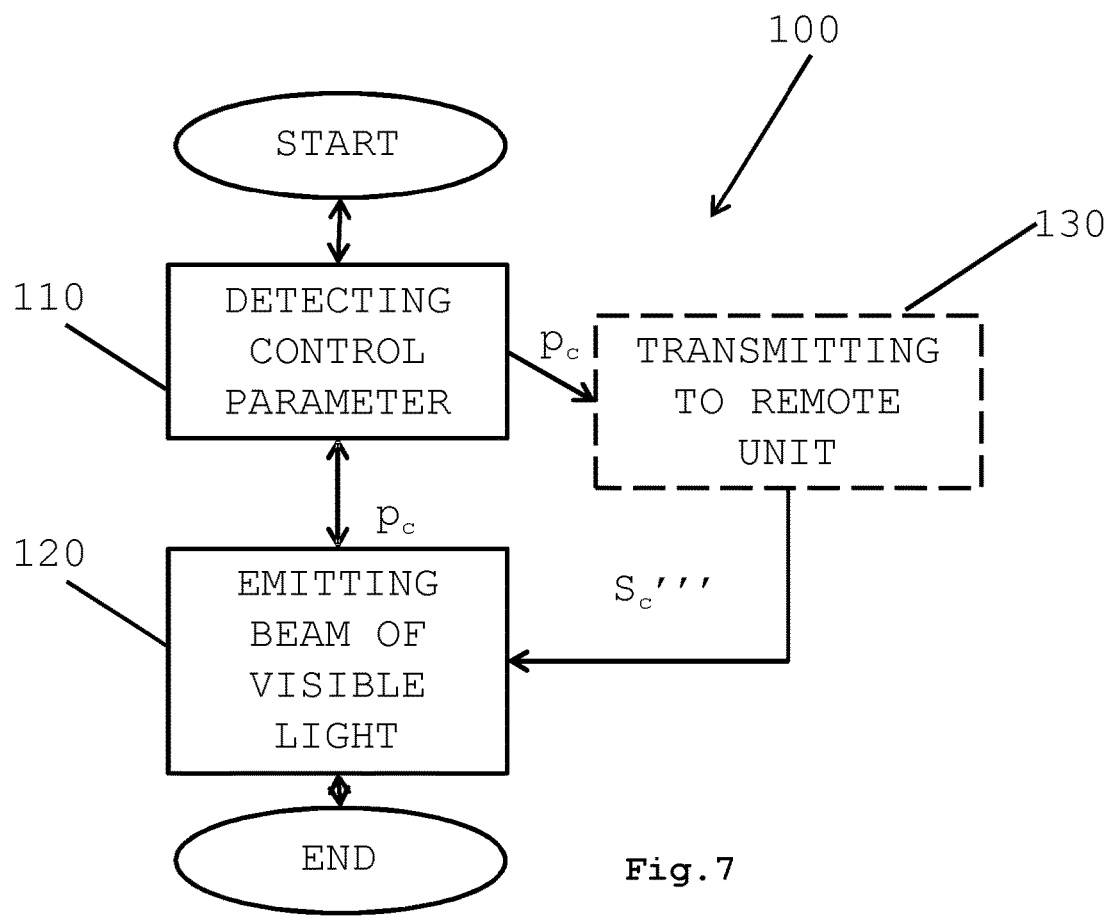
FIGS. 7 and 8 show some flowchart representative of the main steps of the ambulation assistance method according to the present invention.
Figure 8:
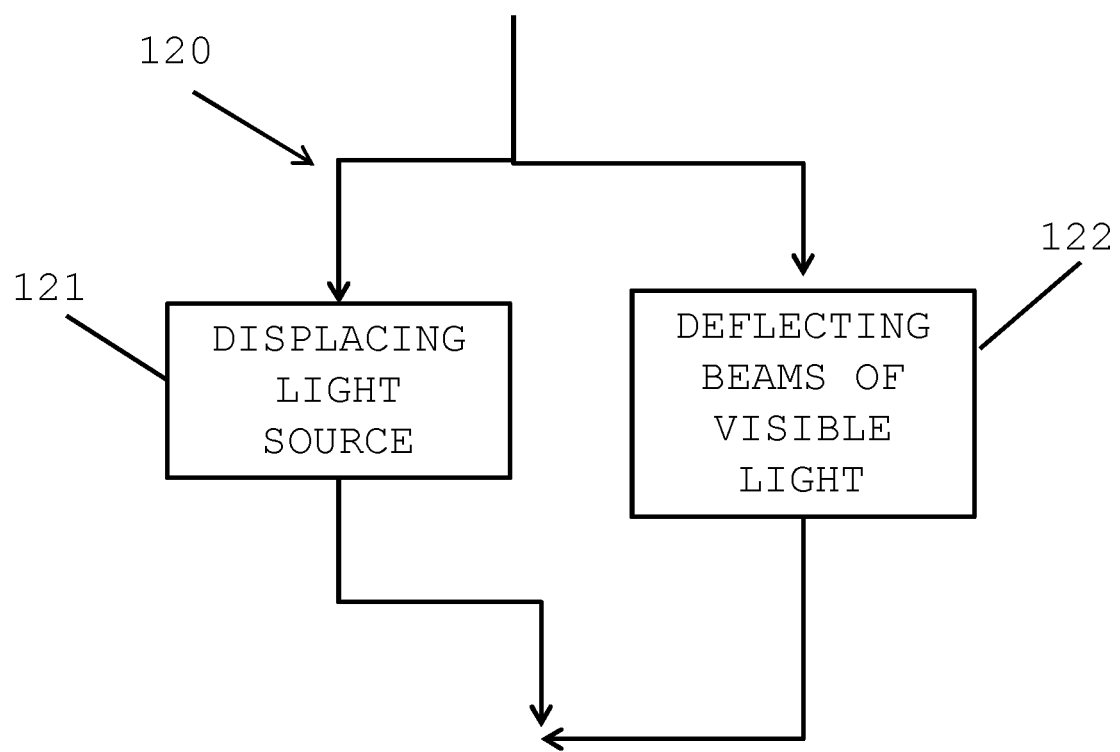

That said, an ambulation assistance method, illustrated in FIG. 7 and denoted on the whole with numeral reference 100, is part of the present invention also, which can be optionally implemented with the device 1 afore described and comprises the following operative steps of:

detecting at least one control parameter ($p_c$) indicating the ambulation condition of a person—step 110; and emitting, as a function of said at least one control parameter $p_c$ detected, at least one beam of visible light 5 towards the ground, at least at one front stepping point (6, 61, 62) next to which a person has to move a foot employed, in that moment, during ambulation—step 120.

Advantageously, the at least one control parameter $p_c$ corresponds to an angle or a displacement measurement that are related to the instant position of at least one part of the body of said person, during ambulation, said part of the body being a lower limb or the waist or torso of such a person.

In case the body part concerned is a lower limb, the control parameter $p_c$ can comprise at least one angle related to the mutual position between femur and tibia of said person, or an angle related to the rotation of the femur with respect to an axis perpendicular to the ground, or else an instant torsion between femur and tibia and/or an angle related to the instant lateral yielding of the knee joint.

In case the body part concerned is the waist or torso of a person, the control parameter $p_c$ can comprise at least one measurement of the displacement of the waist or torso of such a person along the forward direction x-x.

According to such a method, the step 120 of emitting the at least one beam of visible light 5 comprises at least one step of displacing 121 said at least one corresponding light source 4 and/or one step of deflecting 122 said at least one beam of visible light 5 coming out from said at least one light source 4, said displacing step 121 and said deflecting step 122 being executable in sequence, one before the other one or contemporaneously as a function of the value of said at least one control parameter $p_c$.

According to a variation of the method of the present invention, it is advantageously provided that said light source 4 is worn by a person at the knee joint and that the displacing step 121 to displace the at least one light source 4 comprises a sub-step of displacing said at least one light source 4 along a plane crossing the joint of such a knee and diagonal and/or parallel to the forward direction x-x, such that the light source can project said beam of visible light 5 to a front stepping point 6, 61, 62 on the ground, that remains still during the ambulation of the person wearing the light source 4, in the time period in which the person makes a step in the forward direction.

Also the deflecting step, that can optionally be implemented by deflector means of the afore described type, allows the beam of visible light 5 to be oriented along a plane crossing the joint of such a knee and diagonal and/or parallel to the forward direction x-x, to a front stepping point 6 on the ground that remains still, in the time period in which the person makes a step in the forward direction.

According to a variation of the method of the present invention, it is advantageously provided that said light source 4 is worn at the waist or torso and that the displacing step 121 to displace the at least one light source 4 comprises a sub-step of displacing said at least one light source 4 along a plane perpendicular to the ground and crossing the forward direction x-x. Similarly, also the deflecting step, that can optionally be implemented by deflector means of the afore described type, allows the beam of visible light 5 to be oriented along a plane perpendicular to the ground and crossing the forward direction x-x, at a front stepping point 6, 61, 62 on the ground that remains still, in the time period in which the person makes a step in the forward direction.

The method of the present invention provides that said step of emitting said at least one beam of visible light occurs in a continuous or intermittent manner, such that consecutive front stepping points (61, 62) can be outlined on the ground, to which a person has to move the feet during the ambulation.

The method according to the present invention advantageously comprises a step of transmitting said at least one control signal $s_c'''$ related to the control parameter $p_c$, to at least one remote control unit. The remote control unit is arranged for receiving the at least one parameter $p_c$, for processing it and possibly transmitting to said receiving unit at least one control signal $s_c'''$ of said at least one beam of visible light 5 to be emitted.

The person skilled in the art will find not difficult to understand how the control signal $s_c'''$ can be a function of a comparison carried out between said at least one control parameter $p_c$ and at least one reference parameter, where the reference parameter can comprise one or more threshold ranges, which can be defined, for example, based on gender (male or female), age, pathology and other of the person whose ambulation is to be assisted.

As it will be understood, the method of the present invention allows, this way, a control signal $s_c$ of the beam of visible light 5 to be emitted and customized based on the characteristics of the person whose ambulation is to be assisted.

Not only, the afore described method, combined with a device as afore described, allows automatically and during ambulation adjusting the distance between the marks projected by the beam of visible light 5 and the person him/herself, since the step of moving the light source 4, 41, 42 and/or deflecting the beam 5, 51, 52 emitted therefrom can also be controlled remotely by the remote control unit and transceiver unit 12 and/or the processing unit 9.

According to a further characteristic the control unit can comprise means for loading data describing a user ambulation behavior, the data being related to the values of one or more of the control parameters afore described in the various embodiments as a function of time and during ambulation.

These data are loaded into the control unit that defines the position of the marks 7 based on the same data and/or a predetermined ambulation assistance and/or rehabilitation program that can have functionality conservation only and/or improvement aims.

By real time recording the ambulation behavior, thanks to the measurements of the ambulation condition parameter(s), the control unit can real time adapt the mark positioning parameters based on the user progresses and/or difficulties.

In reference to the FIGS. 2, 3, 4, 5 showing a block diagram of the control unit of the device 1, a memory 109 is shown in which a control program is loaded coding the execution instructions of an adaptive algorithm for calculating the control signals of the light source and/or the position to which the mark has to be projected, when the source is combined with or comprises active units for positioning and/or orienting the light beam and that, based on the information of the sensors 8 and/or descriptive parameters of the user ambulation behavior acquired in a prior step of ambulation analysis, calculates the mark projection position and/or changes the same in real time during the use of the device.

The afore described ambulation assistance device and method achieve the objects in the introduction. They allow in fact a mark projected to the ground to be stabilized, during the ambulation, in the time period in which the person makes a step in the forward direction.

They allow supporting the ambulation of both the lower limbs of a person with a single device, allow easily adjusting the distance between the person and the mark projected to the ground, and most of all stabilizing the mark itself. According to the afore described variations, the device 1 according to the invention is able to project a mark 71 for the foot of the lower limb opposite to the one supporting the device and/or a mark 72 for the foot of the lower limb supporting the device and is thus very versatile in its possible applications.

For the sake of clarity, it has to be specified that the afore described method can be partly implemented by a software or firmware stored in a proper memory provided (not illustrated) inside the processing unit 9 and/or the remote control unit and can be run in a continuous loop or not, according to the needs of the case.

Figure 9:
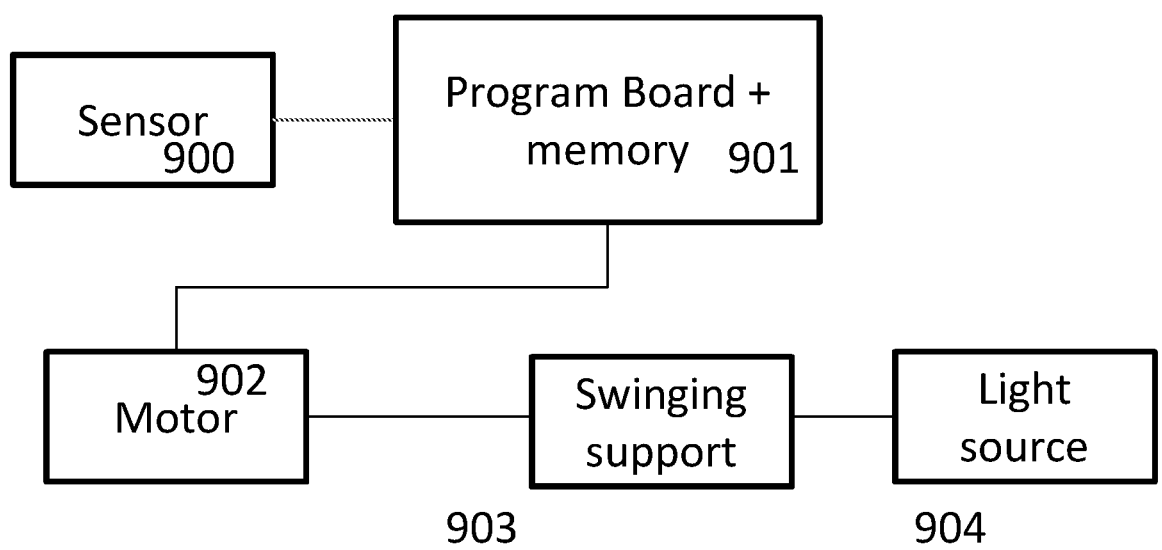
FIG. 9 shows an example of a system for stabilizing the footprint, i.e. the mark generated by the light beam on an incidence plane using a sensor of position and orientation of the light sources, in particular an accelerometer and gyroscopic sensor made with MEMS technology.

In reference to FIG. 9, this shows a variation of the device according to the present invention comprising a system for stabilizing the mark generated by the light beam emitted by the light source on an incidence plane.

According to a first variation, said system is intended to operate to stabilize the mark of the light beam as a function of movements additional to those deriving from the ambulation only and is thus provided in combination with anyone of the preceding embodiments and variations described, preferably for each light source and/or to modify the position and/or orientation of the same or else to modify the settings of the system of optical deflectors in order to change, in both cases, the orientation of the propagation axis of the light beam and to stabilize the position thereof on the incidence plane.

In this case, the program board with memory denoted by 901 can be part of the processing unit that is designed for receiving and processing the measurement signals of the position and/or orientation or the changing of the position and/or orientation of the corresponding light source.

According to an embodiment, the measurement of the position and/or orientation or the changing of the position and/or orientation takes place thanks to a sensor 900 that preferably consists of the combination of at least one accelerometer and one gyroscope.

The measurement signals are processed and transformed in power supply signals of a motor 902 actuating the displacement of the corresponding light source 904. This is mounted on a support 903 swinging about at least one axis, preferably about at least three axes, the support being dynamically connected to the shaft of the motor 902.

Swinging supports of the aforesaid type are known in the state of the art in a wide number of variations, as well as the dynamic connection with motorized shafts for actuating such supports.

According to an embodiment, the sensor 900 is made by using a technique of the so called MEMS type that is the acronym of the Micro Electro Mechanical Systems definition.

Alternatively, so called NEMS, i.e. Nano Electro Mechanical Systems, technologies can be used.

MEMS technology (acronym of Micro Electro Mechanical Systems) allows integrating on the same silicon substrate both electronic circuits and opto-mechanical devices, by using manufacturing technologies similar to those used for making integrated circuits.

The sizes of a MEMS device are generally variable between few microns and one millimeter, while the single components it is composed of vary between 1 and 100 microns. MEMS is an innovative and promising technology that, combining the principles of the silicon based electronic technology with micromachining, allows high integration "smart" devices to be realized on the same chip. Inside each MEMS device (accelerometer—for example) we can figure that there are a "brain" (in practice an integrated circuit) and a set of "arms" and "eyes" by which it is able to monitor and control the external environment. Some micro-sensors (the "eyes") acquire information from the external environment by measuring physical variables such as position, motion, temperature, pressure, magnetic field, and various other types of optical and chemical phenomena. All these information can then be processed by the "brain", which acts on the surrounding environment by means of the "arms", fundamentally micro-actuators.

The NEMS technology is the further reduction of the MEMS technologies to the nanometer scale.

An advantageous embodiment of the present invention provides that the sensor 8 is at the same time also the sensor for detecting a control parameter pc of the ambulation, thus replacing the sensors detecting these parameters of the previous embodiments and significantly simplifying the device realization.

This in fact, thanks to the high integration of the MEMS or NEMS technology and the ease of making the swinging support, allows the device complexity to be significantly reduced, the bulk and weight thereof to be remarkably reduced, thus making it a device of easy and comfortable use and that does not need complex systems for the attachment to the user body.

The processing unit inside the MEMS device also allows transferring to this unit the functions executed by the processing unit described in reference to the previous embodiments, whereby the device is effectively highly practical and easy to use.

The advantage is obtained at the same time of a high stabilization of the mark position, i.e. of the footprint projected by the source on the incidence plane of the light beam.

In the configuration according to this embodiment variation the device according to the present invention is composed of at least one light source generating a beam of light radiation oriented on an ambulation plane, whereby a footprint of said light beam is formed on said plane at least one swinging support of said light source, the support can swing the light source or deviate the direction of the light beam emitted such to change the direction of the propagation axis of the light beam towards the incidence plane and thus the position of the footprint generated by the same;

at least one motor for actuating the angular displacement of the light source a sensor measuring the position and/or orientation of the light source, in reference to the direction of the axis of propagation of the emitted light beam and/or the variation over time of one or both these parameters and the sensor also detecting, at the same time, a control parameter pc identifying the ambulation condition;

a processing unit generating a power supply signal of the motor actuating the angular displacement of said light source as a function of at least one, preferably part or all the aforesaid parameters measured by the sensor, in order to stabilize the position of said footprint during ambulation.

When a single light source is provided, the beam generated by the same is further oriented alternately on the path of the right foot and on the path of the left foot, thanks to the measured parameters.

When two light sources are provided, each one being intended to cooperate with one of the legs, the measurement signals of the afore defined parameters are used also to alternatively switch on and off the light source combined with the right leg and that combined with the left leg.

With the embodiment variations described in reference to FIG. 9, one or more of the further characteristics provided in combination with one or more of the preceding embodiments can be combined, such as for example the use of optical deflectors to change the orientation of the beam alternatively or in addition to the angular displacement of the light source and/or the presence of a receiving/transmitting section through which the devices are connected to a remote station, or a cloud with which data and information are exchanged and/or diagnostic or upgrade activity of the software run by the processing units are run.

Herein and in the following description, as well as in the claims, the word mark is used. With this word the footprint generated by the light beam emitted by a source on the incidence plane of this light beam is meant, for example the ground or an ambulation plane.

Now, the exemplary embodiments of the device and method of the present invention are susceptible of a number of changes and variations, without thereby departing from the protection scope, as defined by the attached claims.

The invention claimed is:

1. An ambulation assistance wearable device, comprising:
a support (2), configured to be removably attached to a body of a person in an attachment position;
a power supply (3), anchored to said support (2);
a light source (4, 41, 42), mounted on said support (2) and electrically connected to said power supply (3), said light source (4, 41, 42) being configured to emit a beam of visible light (5, 51, 52) towards the ground, at least at one front stepping point (6, 61, 62) to which the person has to move a foot to move forward along an ambulation direction (x-x);
a sensor (8) configured to detect at least one control parameter (pc) identifying an ambulation condition; and a processing unit (9), configured to control activation-deactivation of said light source (4, 41, 42) as a function of said at least one control parameter (pc), said processing unit (9) being operatively connected to said power supply (3), said light source (4, 41, 42), and said sensor (8);

wherein:
said at least one control parameter ($p_c$) corresponds to an angle or to a displacement measurement related to an instant position of at least one part of the body of said person, during ambulation;
said light source is mounted on a second, movable support to change an orientation of a propagation axis of the beam of visible light and/or a position of said light source;
said movable support is dynamically connected to a shaft of a motor
said motor is operated by a control unit;
said control unit is designed to receive measurement signals of the position in space of said light source or a change of said position, said control unit being further designed to generate a control signal for operating said motor as a function of said measurement signals of the position of said light source, said control signal being adapted to compensate for a change of the position of said light source.

2. The ambulation assistance wearable device according to claim 1, wherein said sensor comprises a combination of accelerometer and gyroscope.

3. The ambulation assistance wearable device according to claim 1, wherein the sensor further measures the position of the light source and/or the change of the position over time.

4. The ambulation assistance wearable device according claim 3, further comprising a deflector (11) for said beam of visible light (5), at a plane crossing a knee joint and parallel to said forward direction (x-x).

5. The ambulation assistance wearable device according to claim 4, wherein said deflector (11) comprises a system of lenses and/or mirrors, which is configured to receive said beam of visible light (5) emitted by said light source (4) and to transmit said beam towards a ground, said deflector (11) being operatively connected to said processing unit (9) and orientable as a function of the control parameter ($p_c$) transmitted by said processing unit (9).

6. The ambulation assistance wearable device according to claim 5, wherein said at least one control parameter ($p_c$) is a parameter indicating a rotation of a femur with respect to an axis perpendicular to the ground.

7. The ambulation assistance wearable device according to claim 5, wherein said deflector (11) is orientable such that said beam of visible light (5) is splittable in a first beam (51) projectable to the ground in a first front stepping point (61), corresponding to a point to which said person has to move a foot opposite to a point of a lower limb supporting said ambulation assistance wearable device, and a second beam (52) projectable to the ground in a second front stepping point (62), corresponding to the point to which said person has to move the foot of the lower limb supporting said device.

8. The ambulation assistance wearable device according to claim 7, wherein said first beam (51) and said second beam (52) are projectable alternatively, as a function of said at least one control parameter ($p_c$), said at least one control parameter indicating a flexion of the knee joint of a limb supporting said ambulation assistance wearable device.

9. The ambulation assistance wearable device according to claim 1, wherein said attachment position is at a lower limb and wherein said angle is an angle related to a mutual position between femur and tibia of said lower limb.

10. The ambulation assistance wearable device according to claim 1, wherein said attachment position corresponds to a knee joint of a lower limb supporting said ambulation assistance wearable device.

11. The ambulation assistance wearable device according to claim 5, wherein said light source (4, 41, 42) is attached to said support (2) in an external lateral position or an internal lateral position, with respect to a sagittal plane of symmetry of said knee joint or at said sagittal plane of symmetry.

12. The ambulation assistance wearable device according to claim 10, wherein said light source (4, 41, 42) is mounted as movable with respect to said support (2), and wherein said front stepping point (6, 62) corresponds to a point to which the person has to move the foot of the lower limb supporting said ambulation assistance wearable device.

13. The ambulation assistance wearable device according to claim 12, further comprising an actuator (10) that displaces said light source (4, 41, 42) along a plane crossing the joint of knee joint and parallel to said ambulation direction (x-x).

14. The ambulation assistance wearable device according to claim 13, wherein said light source (4) is mounted on said support (2), rotatable about an axis parallel to a transverse axis of said knee joint, and wherein said actuator (10) comprises a rope constrained, on one side, to said light source (4), and on another side, to a waist or thigh of said person, such that said light source (4, 41, 42) is movable as a function of a position of a femur with respect to an axis perpendicular to a ground, during the ambulation along the plane crossing the knee joint and parallel to said forward direction (x-x).

15. The ambulation assistance wearable device according to claim 13, wherein said light source (4, 41, 42) is mounted on said support (2), rotatable about an axis parallel to a transverse axis of said knee joint, and wherein said actuator (10) comprises a mass, supported underneath by said light source (4), such that said light source (4) is movable, due to gravitational force, during the ambulation along the plane crossing the knee joint and parallel to said forward direction (x-x).

16. The ambulation assistance wearable device according to claim 13, wherein said actuator comprises a servo-assisted assembly (8c) between said support (2) and said light source (4), arranged for displacing said light source (4) along the plane crossing the knee joint and parallel to said forward direction (x-x), as a function of the at least one control parameter ($p_c$), sent by said processing unit (9).

17. The ambulation assistance wearable device according to claim 16, wherein said at least one control parameter ($p_c$) is a parameter indicating a rotation of a femur with respect to an axis perpendicular to a ground.

18. The ambulation assistance wearable device according to claim 16, wherein said servo-assisted assembly (8c) between said support (2) and said light source (4), is arranged for displacing said light source along a transverse plane, as a function of said at least one control parameter ($p_c$) sent by said processing unit (9).

19. The ambulation assistance wearable device according to claim 18, wherein said at least one control parameter ($p_c$) is a parameter indicating an instant torsion between femur and tibia and/or an instant lateral yielding of the knee joint.

20. The ambulation assistance wearable device according to claim 1, wherein said light source comprises at least:
a first light source (41), and
a second light source (42).

21. The ambulation assistance wearable device according to claim 20, wherein said first light source (51) and said second light source (52) are comprised of, or comprise, a led strip.

22. The ambulation assistance wearable device according to claim 1, wherein said at least one front stepping point (6, 61, 62) has a circular or elliptical plane shape, or a shape of a foot sole.

23. The ambulation assistance wearable device according to claim 1, wherein said light source (4, 41, 42) is a monochromatic or polychromatic, visible laser light source.

24. The ambulation assistance wearable device according to claim 1, further comprising a transceiver unit (12) operatively connected to said processing unit (9), arranged for receiving and transmitting control signals ($s_c'''$) to/from a remote control unit.

25. The ambulation assistance wearable device according to claim 1, wherein said attachment position is at a waist or torso, and wherein said displacement measurement is a measurement of a displacement of the waist or torso of said person, along said ambulation direction (x-x).

26. The ambulation assistance wearable device according to claim 25, wherein said attachment position corresponds to a central position of the waist or torso of a person.

27. The ambulation assistance wearable device according to claim 25, wherein said light source (4) is mounted as movable with respect to said support (2), and wherein said at least one front stepping point (6, 61, 62) is comprised in a mark (7), generated by said beam of visible light (5), said at least one mark (7) having circular shape symmetrically arranged along said ambulation direction (x-x).

28. The ambulation assistance wearable device according to claim 27, wherein said at least one front stepping point (6, 61, 62) is displaced laterally right or left with respect to said ambulation direction (x-x).

29. The ambulation assistance wearable device according to claim 25, further comprising an actuator (10) operatively connected to said processing unit (9) and said light source (4) and configured, in use, to move said light source (4) along a plane perpendicular with respect to a ground and crossing at least said ambulation direction (x-x).

30. The ambulation assistance wearable device according to claim 25, further comprising a deflector (11) for said beam of visible light (5), said deflector being configured to receive said beam of visible light (5) emitted by said light source (4) and to transmit said beam towards the ground, along a plane perpendicular to the ground and crossing at least said ambulation direction (x-x), said deflector (11) being operatively connected to said processing unit (9) and orientable as a function of the at least one control parameter ($p_c$) transmitted by said processing unit (9).

31. The ambulation assistance wearable device according to claim 30, wherein said at least one control parameter (pc) is a parameter indicating a rotation of a femur with respect to an axis perpendicular to the ground and/or a measurement of an instant displacement of a torso or waist of said person.

32. A method for assisting ambulation of a person, comprising:
detecting at least one control parameter ($p_c$) indicating an ambulation condition of at least one person; and
emitting, as a function of said previously detected at least one control parameter ($p_c$), a beam of visible light (5, 51, 52) by a light source (4, 41, 42) towards a ground, and at least at one front stepping point (6, 61, 62) to which said person has to move a foot employed, in that moment, in the ambulation, wherein said at least one control parameter ($p_c$) corresponds to an angle or to a displacement measurement related to an instant position of at least one part of a body of said person, during ambulation;

measuring a position in a space of the light source and an orientation thereof in reference to a direction of propagation of a light beam emitted therefrom; and changing an orientation of the light source in reference to a direction of propagation of the light beam emitted as a function of measurement values of position and orientation of said light source such to hold steady the position on an incidence plane of a footprint generated by the light beam emitted by the light source.

33. The method according to claim 32, wherein said at least one control parameter is influenced by:
a rotation of a femur of a lower limb of said person, with respect to an axis perpendicular to a ground,
an instant torsion between femur and tibia of said lower limb, and/or
an instant lateral yielding of a knee joint of said lower limb;
or said at least one control parameter is influenced by a displacement measurement of a waist or torso of said person, during ambulation along a forward direction (x-x).

34. The method according to claim 33, wherein emitting the beam of visible light (5, 51, 52) comprises displacing the light source (4, 41, 42) and/or deflecting said beam of visible light (5, 51, 52) coming out from said light source (4, 41, 42), said displacing and said deflecting being executable automatically in sequence, one before the other or contemporaneously as a function of a value of said at least one control parameter ($p_c$), said beam of visible light being directed to a respective front stepping point (6, 61, 62) to the ground so as to remain still, during ambulation, in a time period in which said person lifts a foot to bring the foot at said at least one front stepping point.

35. The method according to claim 34, when said light source (4, 41, 42) is worn by a person at a knee joint, wherein step of displacing comprises at least one sub-step of displacing said light source (4, 41, 42), along a plane crossing a knee joint and diagonal and/or parallel to said forward direction (x-x), such that said light source projects said beam of visible light (5, 51, 52) in a corresponding front stepping point (6, 61, 62), so as to remain still, during the ambulation of the person wearing said light source (4, 41, 42), in a time period in which said person makes a step in the forward direction (x-x).

36. The method according to claim 32, wherein said light source (4, 41, 42) is worn by the person at a knee joint, wherein deflecting comprises at least one sub-step of deflecting said beam of visible light (5, 51, 52) along a plane crossing the knee joint and diagonal and/or parallel to said forward direction (x-x), such that said beam of visible light (5, 51, 52) is projectable in a corresponding front stepping point (6, 61, 62), to a ground, said front stepping point remaining still, during the ambulation of the person wearing said light source (4, 41, 42), in a time period in which said person makes a step in the forward direction.

37. The method according to claim 32, wherein said light source (4) is worn by the person, at a waist and/or torso, wherein displacing the light source (4) comprises a sub-step of displacing said light source (4) along a plane substantially perpendicular to a ground and crossing said forward direction (x-x).

38. The method according to claim 32, wherein said light source (4) is worn by the person at a waist and/or torso, wherein deflecting comprises at least one sub-step of deflecting said beam of visible light (5) along at least one plane substantially perpendicular to a ground and crossing said forward direction (x-x), such that said beam of visible light (5) is projectable in a corresponding front stepping point (61, 62), to the ground, so as to remain still, during the ambulation of the person wearing said light source (4), in a time period in which said person makes a step in the forward direction.

39. The method according to of claim 32, wherein the step of emitting said beam of visible light (5, 51, 52) occurs in a continuous or intermittent manner.

40. The method according to claim 32, further comprising a step (130) of transmitting said at least one control parameter ($p_c$) to a remote control unit and of receiving at least one control signal ($s_c'''$) of said beam of visible light (5, 51, 52) as a function of an analysis performed by said remote control unit.

41. The method according to claim 40, wherein said analysis comprises at least one comparison between said at least one control parameter (pc) and at least one reference parameter, and wherein said at least one reference parameter comprises one or more threshold ranges based on gender, age and pathology of said person.

* * * * *